United States Patent [19]

Miller et al.

[11] Patent Number: 4,874,368

[45] Date of Patent: Oct. 17, 1989

[54] FIBRIN GLUE DELIVERY SYSTEM

[75] Inventors: Curtis H. Miller, Burnsville, Minn.; I. Kaufman Arenberg; John H. Altshuler, both of Englewood, Colo.

[73] Assignee: Micromedics, Inc., St. Paul, Minn.

[21] Appl. No.: 224,078

[22] Filed: Jul. 25, 1988

[51] Int. Cl.[4] ............................................. A61M 5/08
[52] U.S. Cl. .................................... 604/82; 222/137; 604/191
[58] Field of Search ................. 604/82, 191; 222/129, 222/137, 145

[56] References Cited

U.S. PATENT DOCUMENTS

| | | | |
|---|---|---|---|
| 2,533,004 | 5/1950 | Ferry et al. | 260/112 |
| 3,467,096 | 9/1969 | Horn | 604/191 X |
| 3,828,980 | 8/1974 | Creighton et al. | 604/191 X |
| 4,040,420 | 8/1977 | Speer | 604/82 |
| 4,359,049 | 11/1982 | Redl | 604/191 X |
| 4,735,616 | 4/1988 | Eibl et al. | 604/191 |

FOREIGN PATENT DOCUMENTS 25913 2/1884 Fed. Rep. of Germany ...... 604/191

Primary Examiner—Dalton L. Truluck
Attorney, Agent, or Firm—Orrin M. Haugen; Thomas J. Nikolai; Frederick W. Niebuhr

[57] ABSTRACT

An improved fibrin glue delivery system is disclosed. The delivery system is comprised of a pair of syringe tubes which can be actuated by plungers simultaneously or independently, a connecting member which holds the syringe tubes in parallel alignment and a unique needle assembly which ensures the components in the syringe bodies will not be comingled until they reach the treatment site. The unique needle assembly also permits the user to manipulate the needles to enhance visibility when the surgeon is working through a speculum or when direct access is difficult.

3 Claims, 1 Drawing Sheet

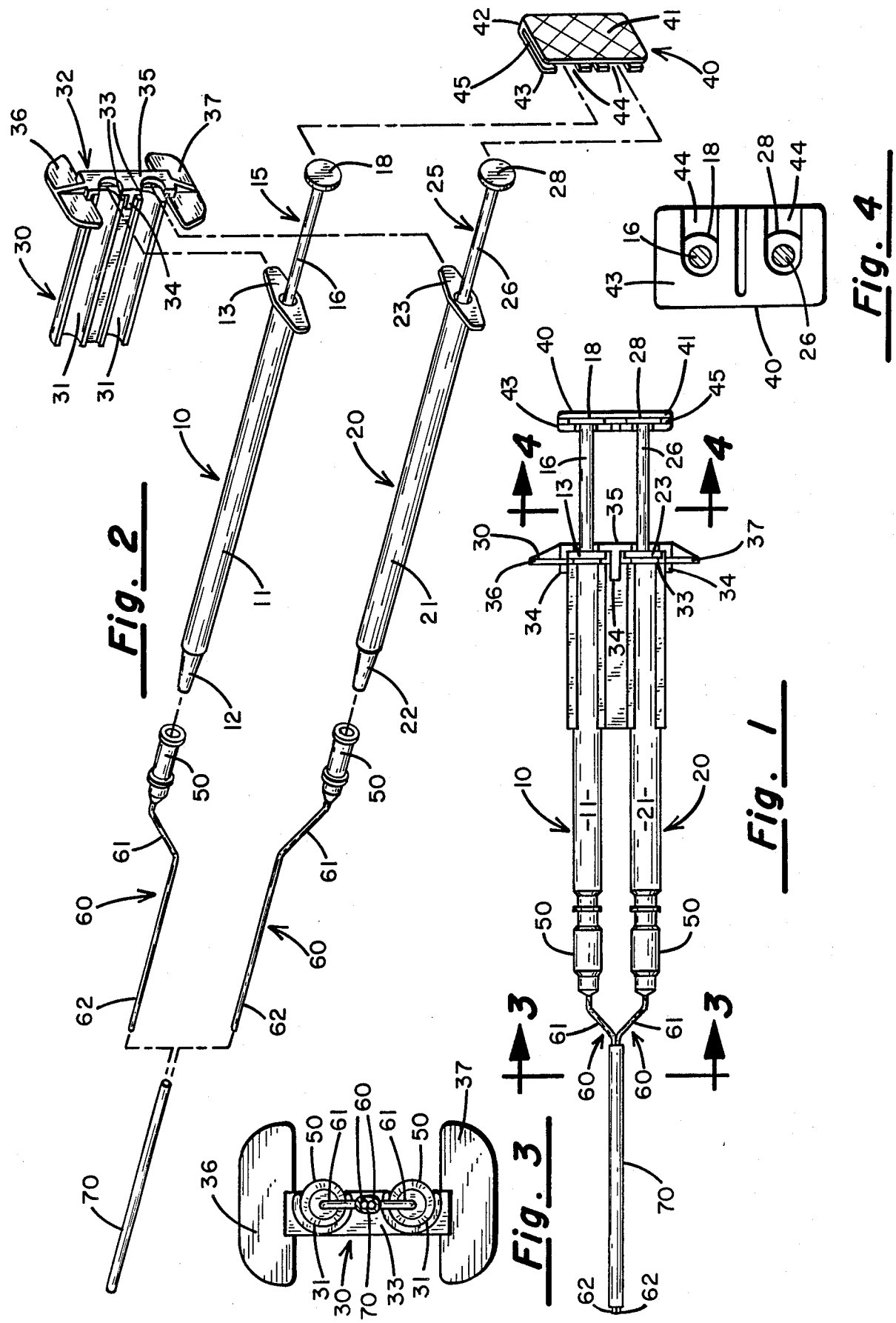

FIBRIN GLUE DELIVERY SYSTEM

BACKGROUND OF THE INVENTION

The present invention relates to a tissue adhesive and a delivery system for applying the same. More particularly, the tissue adhesive is comprised of a first solution containing fibrinogen and a second solution containing thrombin. The apparatus is used to keep these two solutions separate until they are applied together at a treatment site to seal a wound, stop bleeding or the like.

Fibrin glues and adhesives have been known for many years. For example, U.S. Pat. No. 2,533,004 which issued on Dec. 5, 1950 to John D. Ferry discloses various methods for making fibrin clots using different concentrations of fibrinogen solution in conjunction with the thrombin solution.

Similarly, various types of applicators for fibrin glue solutions are disclosed in the prior art. For example, U.S. Pat. No. 4,359,049, which issued on Nov. 16, 1982 to Redl, et al, discloses a syringe-type apparatus for applying a tissue adhesive. The apparatus disclosed in the Redl patent includes a plurality of standardized one-way syringe bodies of synthetic material. Each syringe body accommodates a plunger and ends in a coni. The apparatus also includes a means for holding the various syringe bodies together, a guide rod, common actuating means associated with the guide rod and the plungers, and a collecting head connecting the coni of said syringe bodies.

The design of the Redl patent, however, is lacking for several reasons. First, the connecting head brings the two materials together and the materials then travel together through a single mixing needle. Because the materials are so quick to form a bond, this arrangement can cause the apparatus to become clogged and unusable. Second, the apparatus of the Redl et al fails to provide a means by which the apparatus can be gripped comfortably in a variety of orientations. Thus, it is not as easy to manipulate as may be necessary for use in certain surgical procedures.

The Eibl et al 4,735,616 patent which issued on Apr. 5, 1988 describes another arrangement for applying a tissue adhesive. The applicator of Eibl et al is quite similar to the applicator of Redl et al discussed above and, therefore, is subject to the same deficiencies. The primary differences between the Eibl et al and Redl et al disclosures is that the Eibl system includes one syringe body that has a cross-sectional area that is two to nine times larger than the cross-sectional area of the remaining syringe bodies. This permits disproportionate amounts of the solutions within the syringe bodies to be dispensed simultaneously. This same feature for this same purpose is also taught in U.S. Pat. No. 4,040,420 to Speer. Also, the Eibl patent discloses bypass means associated with the syringe bodies.

The Speer patent also discloses an embodiment that would help avoid the clogging problems of the Eibl et al and Redl et al patents. However, the apparatus disclosed in the Speer patent would be far more clumsy to work with than the present invention. This is particularly true when the apparatus is to be used in micro surgical procedures such as in the middle or inner ear. Speer, like the other references, fails to teach an acceptable applicator which is comfortable to hold in a plurality of orientations and, therefore, easy to manipulate.

SUMMARY OF THE INVENTION

The present invention is directed toward avoiding the disadvantages and difficulties described above. Its principal object is to provide a fibrin glue delivery system which is inexpensive to manufacture, designed so that it can be gripped comfortably and manipulated in a variety of orientations, capable of providing the fibrin glue products to the treatment site with precision, and not subject to becoming clogged. Another object of the invention is to provide such a device which permits either simultaneous or independent application of the glue products as desired. Still another object is to provide such a device which incorporates a needle assembly which is separable from the rest of the unit. This permits the needles to be packaged separately allowing the physician to choose between a variety of needle sizes and shapes. It also reduces overall inventory costs and permits the components to be more effectively sterilized so that the surgical team can prepare the glue components and assemble the dispenser in the operating room.

The object of the present invention is achieved by providing an apparatus comprised of a pair of syringe bodies which are held in parallel relationship with respect to one or another by a clamp which is specially designed to have flanges which project to form an effective means by which the physician can comfortably hold the dispenser in a variety of orientations. Further, to prevent undue clogging of the delivery system, the conis of the individual syringe bodies are connected to an adapter head. Projecting from each adapter head is a separate needle. These separate needles are bent so that they come together and have elongated sections which are parallel to each other. A plastic tube surrounds the parallel sections of the needles to hold them together. When the apparatus is so constructed, there is no comingling of the solutions which form the fibrin glue upstream from the treatment site. Further, the device is particularly suited for micro surgical applications because of the elongated narrow needle sections.

BRIEF DESCRIPTION OF THE DRAWINGS

FIG. 1 is a plan view of the apparatus of the present invention;

FIG. 2 is an exploded perspective view of the apparatus of the present invention showing the individual components;

FIG. 3 is a cross sectional view of said apparatus through Line 3—3 in FIG. 1; and FIG. 4 is a cross sectional view of the apparatus through Line 4—4 in FIG. 1.

DETAILED DESCRIPTION OF THE PREFERRED EMBODIMENT

As best shown in FIG. 1, the apparatus of the present invention is comprises of a pair of syringe bodies 10 and 20 which are held together by a connecting member 30. Associated with each of the syringe bodies 10 and 20 is a piston type plunger 15 and 25 respectively. Each of the piston type plungers has a push flange (18 and 28) which are held together by a connecting clip member 40 so that the two pistonplungers can be actuated simultaneously.

The apparatus also includes a separate connector 50 associated with each of the syringe bodies. Connectors 50 are used to attach a needle 60 to the syringe body. Each of these needles 60 is bent to have a centering section 61 and an elongated section 62. When the apparatus is assembled, the centering sections of the needles align sections so they run parallel to each other and touch. Finally, the apparatus includes a plastic hollow sleeve 70 which receives each of the needles along their elongated sections to hold the needles together in the desired relationship.

The syringe bodies 10 and 20 are typically standard off-the-shelf products available through many manufacturers. Preferably, the syringe bodies are composed of a hollow tube (11 and 21) which has a coni (12 and 22) at one end and a flange (13 and 23) at the other end. The syringe bodies 10 and 20 can be of the same diameter if it is desirable to dispense the solution from each tube simultaneously at the same rate. Likewise, the syringe bodies 10 and 20 can have different predetermined effective diameters to facilitate the simultaneous application of differing predetermined amounts of the two solutions.

As stated above, associated with each of the syringe bodies is a piston type plunger. Each of the plungers (15 and 25) has an elongated shaft (16 and 26), a cylindrical head (not shown) which has an ouside diameter slightly less than the inside diameter of the associated syringe body, and a push flange (18 and 28). The overall length of the plungers 15 and 25 are, preferably, the same.

To aid simultaneous actuation of the plungers with equal stroke, the connecting clip member 40 may be secured to each of the push flanges 18 and 28. Clip member 40 has a unique configuration which permits it to be slipped on an off the push flanges 18 and 28 as desired by the surgeon. As a result, the plungers can be actuated simultaneously or separately as desired.

Clip member 40 is preferably comprised of a solid top member 41 which is rectangular in shape, one or more side members 42 projecting downwardly from at least one, but less than all, of the sides of top member 41 and a base member 43, which projects from the side member(s) 42 and is parallel to the top member 41. The gap 45 between the base member 43 and the top member 41 is made larger than the thickness of the push flanges 18 and 28. Further, the base member includes two slots 44 for receiving said push flanges. Slots 44 are proportioned so they are larger than the diameter of shafts 16 and 26, but smaller than the diameter of the push flanges 18 and 28. This configuration permits the push flanges to be clipped within and retained by member 40 so the two plungers are actuated simultaneously.

Another important feature of the present invention is connecting member 30. The connecting member 30, which can be made of a molded plastic, has two open faced semi-cylindrical channels 31. The channels 31 are formed to receive and retain the syringe bodies 10 and 20 in a parallel alignment. Since the channels 31 are open faced, it is also possible to view the amount of material remaining in the syringe bodies 10 and 20. the holder also includes a unique flange assembly 32. This flange assembly 32 includes a bottom support 33 which is integrally molded with one end of the semi-cylindrical channels 31, a plurality of struts 34, and a top support 35. These struts 34 separate supports 33 and 35 by a distance larger than the thickness of flanges 13 and 23 of the syringe bodies so that said flanges can be received and retained by supports 33 and 35 and struts 34.

Top support 35 includes a pair of flange members 36 and 37 which, because of their unique configuration, provide a means by which the apparatus can be gripped comfortably by a physician in any number of angular orientations. Flange members 36 and 37, combined, project in a plane which is perpendicular to the semicylindrical channels in all directions from said channels. The connecting member 30, therefore, permits the apparatus to be comfortably held between the fingers in a position which is essentially perpendicular to the fingers at essentially any rotational orientation with respect to the fingers. This is particularly important for the precise and delicate application of the fibrin glue.

Also of primary significance are the means by which the fibrin glue components are transferred from their respective syringe bodies to the treatment sites. As indicated above, connectors 50 are used to attach needles 60 to the conis 12 and 22 of the syringe bodies. Connectors 50 have a central lumin therethrough which is in communication with each interchamber of the syringe body and the lumin of the needle 60 associated with the connector. Since there is a separate connector 50 and needle 60 for carrying each material from its syringe body directly to the treatment site, there is no co-mingling of the fibrin glue solutions until they reach the treatment site. As a result, there is no clogging of the dispenser which was an inherent problem with the fibrin glue dispenser of the prior art.

Also, since the separate needles 60 each have an elongated section which is passed through the hollow sleeve 70, they form a structure which permits the surgeon to bend the needles simultaneously to form a desired shape. This feature is desirable to enhance visibility when the surgeon is working through a speculum or where direct access is difficult.

When in use, one of these syringe bodies is filled with a fibrinogen solution and the other syringe body is filled with a thrombin solution. The adaptors are then attached to the conis of each of the syringe bodies. The needles are, of course, held in parallel alignment by the plastic retaining tube which surrounds them. The apparatus then permits the two solutions to be expelled from the end of the needle simultaneously or separately as desired by actuation of the plungers associated with the syringe bodies.

What is claimed is:

1. A delivery system for applying to a treatment site a tissue adhesive having a pair of components which must be kept separate from each other until they reach the treatment site, said delivery system comprised of:
   (a) a first syringe body for storing a first tissue adhesive component and a second dyringe body for separately storing a second tissue adhesive component;
   (b) a separate piston type plunger, having an elongated shaft, a head and a push flange, associated with each of said syringe bodies for expelling from each of said syringe bodies its associated tissue component;
   (c) a hypodermic needle, having an elongated portion, associated with each of said syringe bodies;
   (d) means for connecting said syringe bodies to said hypodermic needles so that each of said tissue adhesive components is afforded an independent flow path from its syringe body, through said connecting means and through its hypodermic needle preventing the comingling of said first and second tissue adhesive components before they reach the treatment site;
   (e) a hollow sleeve surrounding the elongated portions of said hypocermic needles retaining said elongated portions in parallel registration with respect to each other and forming a structure which permits the needles to be bent simultaneously into a desired shape; and (f) means for retaining said syringe bodies in parallel alignment.

2. The apparatus of claim 1 further including a removable connecting clip member to be secured to each push flange so that each piston type plunger may be actuated simultaneously when desired.

3. The apparatus of claim 1 wherein said means for retaining said syringe bodies in parallel alignment includes:

(a) open faced semi-cylindrical channels for receiving and retaining said syringe bodies; and (b) a flange assembly including flange members which project in a plane perpendicular to the semi-cylindrical channels so that the apparatus can be comfortably held by the user in a variety of orientations.

* * * * *